United States Patent
Schafer

(10) Patent No.: US 8,518,681 B2
(45) Date of Patent: Aug. 27, 2013

(54) SELECTIVE LYSING OF CELLS USING ULTRASOUND

(75) Inventor: Mark E. Schafer, Lower Gwynedd, PA (US)

(73) Assignee: Sound Surgical Technologies LLC, Hayward, CA (US)

(*) Notice: Subject to any disclaimer, the term of this patent is extended or adjusted under 35 U.S.C. 154(b) by 157 days.

(21) Appl. No.: 12/941,868

(22) Filed: Nov. 8, 2010

(65) Prior Publication Data

US 2011/0166551 A1    Jul. 7, 2011

Related U.S. Application Data

(60) Provisional application No. 61/266,867, filed on Dec. 4, 2009.

(51) Int. Cl.
    C12N 13/00    (2006.01)
(52) U.S. Cl.
    USPC .................. 435/173.7; 435/173.1; 435/325
(58) Field of Classification Search
    USPC .................................... 435/173.7, 173.1, 325
    See application file for complete search history.

(56) References Cited

U.S. PATENT DOCUMENTS

| | | |
|---|---|---|
| 4,713,053 A | 12/1987 | Lee |
| 4,886,491 A | 12/1989 | Parisi et al. |
| 5,236,414 A | 8/1993 | Takasu |
| 6,071,480 A * | 6/2000 | Halaka ............................ 422/128 |
| 6,686,195 B1 | 2/2004 | Colin et al. |
| 6,777,231 B1 | 8/2004 | Katz et al. |
| 7,226,446 B1 | 6/2007 | Mody et al. |
| 2006/0051865 A1* | 3/2006 | Higgins et al. ................ 435/366 |
| 2009/0171251 A1 | 7/2009 | Rybyanets et al. |
| 2011/0313345 A1 | 12/2011 | Schafer |
| 2013/0012927 A1 | 1/2013 | Schafer |

FOREIGN PATENT DOCUMENTS

EP    1046394 A2 * 10/2000

OTHER PUBLICATIONS

Marentis et al., Ultrasound in Medicine & Biology, vol. 31, No. 9, p. 1265-1277, 2005.*
Cinti et al., Adipose Tissue and Adipokines in Health and Disease, p. 5, Fantuzzi ed., Humana Press, 2007.*
Miller et al., Ultrasound in Medicine & Biology, vol. 30, No. 10, p. 1263-1267, 2004.*
Petersson et al., Analyst, vol. 129, p. 938-943, 2004.*
European Communication in Application 11784380.5, mailed Jan. 8, 2013, 2 pgs.
PCT International Search Report and Written Opinion in International Application PCT/US201/1037562, mailed Feb. 9, 2012, 9 pgs.
Hawkes, J.J. et al., "Microparticle manipulation in millimeter ultrasonic standing wave chambers", Ultrasonics, 36(9), Aug. 1998, pp. 925-931.
PCT International Search Report and Written Opinion in International Application PCT/US2010/058880, mailed Aug. 23, 2011, 10 pgs.

* cited by examiner

*Primary Examiner* — Susan Hanley
*Assistant Examiner* — Damon B Bowe
(74) *Attorney, Agent, or Firm* — Wood, Herron & Evans, LLP

(57) ABSTRACT

Described are embodiments that employ ultrasonic energy to selectively lyse larger adipose cells in a suspension containing adipose cells of different sizes resulting in a suspension in which the only viable cells are the small adipose cells and stem cells. Embodiments provide for generating an acoustic standing wave field of sufficient intensity and proper geometry, that high shear stress is induced on the cell membranes of cells larger than a predetermined size. The remaining small adipose cells can be physically separated from the suspension after the suspension is subjected to the acoustic standing wave field.

16 Claims, 6 Drawing Sheets ered to isolate the stem cells must be performed in a sterile environment.

SELECTIVE LYSING OF CELLS USING ULTRASOUND

I. CROSS-REFERENCE TO RELATED APPLICATIONS

This application claims priority to U.S. Patent Application Ser. No. 61/266,867, filed Dec. 4, 2009 entitled "SELECTIVE LYSING OF CELLS USING ULTRASOUND," the contents of which are hereby incorporated by reference in their entirety as if set forth herein in full.

II. FIELD OF THE INVENTION

Embodiments of the present invention relate to methods and devices for use in the selective "lysing," i.e., destroying, of cells using ultrasound. In particular, the embodiments relate to the selective termination of larger, generally older, adipose cells in a mixture of adipose cells of various sizes and maturities such as found in an extract from animal, e.g., human, tissues.

III. BACKGROUND OF THE INVENTION

When fat cells are extracted from the body, typically in a liposuction procedure, they encompass a range of sizes, from less than 25 microns in diameter, to more than 100 microns in diameter. The smaller cells are typically pre-adipocytes, while the larger cells are fully mature adipocytes. Many of the extracted adipose cells are "alive," i.e., they survive separation from the surrounding tissue and the extraction process. Information suggests that when the extraction process is performed using ultrasonic assisted lipoplasty (UAL) (such as that performed using the VASER® UAL system commercially available from Sound Surgical Technologies LLC in Louisville, Colo.), a greater portion of the extracted cells are alive and can survive for a limited period of time post-extraction. The extracted cells are of interest in several applications.

In the practice of medicine, it is sometimes desired to re-inject the extracted adipose cells into the same patient for purposes of filling or augmenting body locations, e.g., plastic surgery, body sculpting or enhancement. To optimize that process it is helpful to re-inject only live cells. Further, it would be preferable to inject only the smaller cells, preferably the pre-adipocytes. This is because the pre-adipocytes more readily adapt to the re-implantation process, and also stimulate the production of the vascular structure necessary for successful grafting, through the expression of vascular growth factors. The more mature cells, on the other hand, do not generally express the vascular growth factors, and are more likely to undergo necrosis after re-implantation. It is therefore desirable to separate the mature fat cells from the liposuction aspirate before re-implantation. Further, it may be desired to destroy the mature fat cells, so that the only viable cells remaining are of the smaller, more active type. While an exact cut-off size which is optimal for re-insertion has not been clinically established, generally, it would be desirable to lyse those cells larger than about 50 microns. However this may be considered on a patient-by-patient basis, for instance, depending upon the total amount of fat available for re-implantation, the amount required to be re-implanted in order to produce the desired result, the general condition of the patient's cells, etc.

Secondly, it has now been found that stem cells can be derived from adipose cells, a discovery having significant implications for medical research regarding both humans and animals. (See, for example, U.S. Pat. No. 6,777,231 for "Adipose-Derived Stem Cells and Lattices," issued on Aug. 17, 2004.) Young adipose cells are prime candidates for the derivation of stem cells. Stem cells are generally in the range of 15-25 micron in diameter.

Stem cells can be used to regenerate human or other animal tissue. Once isolated, stem cells can be reintroduced into a human or other animal to regenerate tissues, in vitro. Because stem cells may be reintroduced into a human body, processing performed to isolate the stem cells must be performed in a sterile environment.

Thus, it would be desirable to be able to isolate the younger, smaller cells from adipose tissue extracted from humans and other animals and easily maintain a sterile environment for the stem cells to be safely re-injected into a patient.

It is further desirable that this selection, separation, and/or destruction process be accomplished in a rapid manner, as the time between "aspiration" (i.e., removal of tissue from the body via suction) and re-implantation or storage for research should be kept to a minimum.

Prior efforts in this area have involved centrifugation, which does not precisely segregate cells of different sizes. Successful centrifugation also requires a precise drawing off of the centrifuged material, which requires additional handling. Filtering of the aspirate is also possible, although this can also be a time consuming process, and can also cause damage to the cells of interest as they pass through the filter material. Also, since cells are often aggregated in the aspirate and not singulated, it is likely that a cluster of the desired, smaller cells would be filtered out. For example, a cluster of more than a few 50 micron diameter cells would be filtered out by a filter with a 150 micron mesh, which defeats the purpose of the entire filtering process. The use of filtering and/or centrifugation also requires the use of additional devices that must be sterilized to avoid contaminating the stem cells.

Thus, neither centrifugation nor filtering has completely solved the problem of isolating smaller, younger adipose cells. Centrifugation does stratify the aspirate material, with smaller, denser cells at the bottom, and larger, less dense cells at the top of the centrifuge tube. However, the stratification is imprecise; it can be affected by clustering of the cells; and it can cause damage to the desired cells by both additional handling and the stresses of centrifugation.

Similarly filtering the aspirate is also imprecise in that the tendency of cells to be in clusters affects the filtering process.

Accordingly, a need still exists for an improved method of isolating younger adipose cells from an aspirate mixture and maintaining the sterility of the aspirate mixture.

IV. SUMMARY OF THE INVENTION

The summary is provided to introduce aspects of some embodiments of the present invention in a simplified form, and is not intended to identify key or essential elements of the claimed invention, nor is it intended to limit the scope of the claims.

Embodiments of the present invention employ ultrasonic energy to selectively lyse larger adipose cells in a suspension containing adipose cells of different sizes resulting in a suspension in which the only viable cells are the small adipose cells. The embodiments also provide for easily maintaining the sterility of the suspension during lysing by using a cartridge as the chamber for holding the suspension when it is being lysed. The cartridge, in some embodiments, is used only a single time, which reduces the risk of introducing contaminants into the suspension. As used herein "lysis" refers to the destruction of cells, a process that frequently involves disruption of the cell membrane. Thus, the lysed cells spill their internal lipids into the suspension. As a result, the remaining small adipose cells can be physically separated from the suspension.

As used herein, "adipose cells," "fat cells," or "adipocyte" refers to any of various cells found in animal tissue that are specialized for the storage of fat.

Acoustic standing waves have been used to move and sort particles both in air and in liquids. In general, these systems have operated in a different way from embodiments of the present invention and have resulted in acoustic separation, but not lysing.

In designing prior art systems, the selection of the acoustic standing wave field spacing and therefore the selection of frequency and chamber size, are dictated by fluidics issues, not necessarily cell size. Specifically, these prior systems were designed to provide as much physical separation of cells as possible, so that cells of different characteristics that are influenced by acoustics (e.g., compressibility and density) are as far from each other in the flow stream as possible. This simplified the downstream task of bifurcating the flow and having each flow stream have only one cell type. The design of the system parameters, i.e. acoustic standing wave distance, operating frequency, flow rate, dwell time, and chamber size, did not take into consideration the size of the cell nor the forces required to create lysing in the way that is presented here.

The prior art attempted to have all the cells of a specific type or some acoustically differentiable characteristic in a single zone, and all the cells of a different characteristic in another zone, so that the two cell types could be easily separated by separation of the flow streams containing the different zones.

In contrast, embodiments of the invention described herein do not use ultrasonic energy to cause physical separation of cells with different acoustic attributes. Instead, the design rules of the present embodiments are intended to lyse cells above a particular size thereby enabling the subsequent separation of the lysed cell remnants from the unlysed cells without reference to "zones," i.e., flow separation distances. Thus, for example, the embodiment of the present invention illustrated in FIGS. 3 and 4, has cells of different characteristics (in this case, different sizes) all intermixed both before and after the application of ultrasonic energy. To accomplish this result embodiments of the present invention employ standing wave nodal distances which are much smaller than those of the prior art. The large standing wave nodal distances, as described in the prior art, are much larger than the cut-off diameter that would be useful in the present embodiments. In addition, embodiments of the invention described herein include multiple standing wave regions, which would not be useful in a cell separation device.

It should be also noted that unlike nearly every other cell in the body, normal, healthy adipose cells can vary in size over a wide range. This is very different from the case often described in the prior art, in which different cell types, e.g. erythrocytes and adipocytes, are to be separated. Erythrocytes, for example, all are within a very narrow size range of 6-8 micron. Because they are very small and very dense, these cells have a high acoustic contrast compared to blood serum and other cells. Thus, they can be separated relatively easily by the prior art techniques. Those same techniques would be far less effective, if at all, on typical mixtures of adipose cells.

Embodiments of the present invention provide for a new method including the lysing of cells above a given size using the operative principle of generating an ultrasonic standing wave field of sufficient intensity and proper geometry, that high shear stress is induced on the cell membranes. The geometry of the standing wave must be such that the distance between alternating regions of pressure (particle velocity) fluctuation, i.e. one half the wavelength of the sound wave, is the same or smaller than the diameter of the cell size to be lysed. The shear stress is generated by having the cell resident in both regions of alternating pressure (particle velocity), which results in the shear stress being induced upon the cell. This shear stress acts on the cell membrane to the point of causing cell lysis. Cells smaller than the distance between the alternating regions of pressure (particle velocity) fluctuation will only be subjected to isotropic compression and rarefaction, which will not induce shear stress, and will not lyse the cell.

The exact ultrasound pressure levels required to cause lysis of the desired cells depend upon a number of factors, including the viscosity of the surrounding medium, the frequency chosen, the presence of other cells, such as red blood cells, within the medium, the temporal duration of the exposure (dwell time), and is best determined using the guidelines supplied elsewhere herein. In general, the pressure levels will be on the order of kilopascals to Megapascals. Note, however that excessive pressure levels can lead to the onset of cavitation within the fluid, which may act to lyse all the cells within the exposure region irrespective of size.

To be effective in lysing the cells, sufficient stress must be created by the ultrasound energy such that it disrupts the cell membrane, rather than less intense ultrasound pressure levels that may distort but not interrupt the membrane surface. Prior art system which disclosed acoustic means for cell separation used limited ultrasound pressure levels in order to preserve cell integrity.

The small, young, viable cells remaining after the lysing can be separated from the lysed cells as described herein and then re-inserted into the patient using techniques commonly used in current medical procedures and known to one of ordinary skill in the art.

If stem cells are desired, the size differentiation for lysing is set at a smaller level so that only the smallest, i.e., preadipocyte, cells survive the lysing process. These cells are further separated from the suspension to isolate those for stem cell processing.

V. BRIEF DESCRIPTION OF THE DRAWINGS

VI. DETAILED DESCRIPTION OF THE INVENTION

Figure 1:
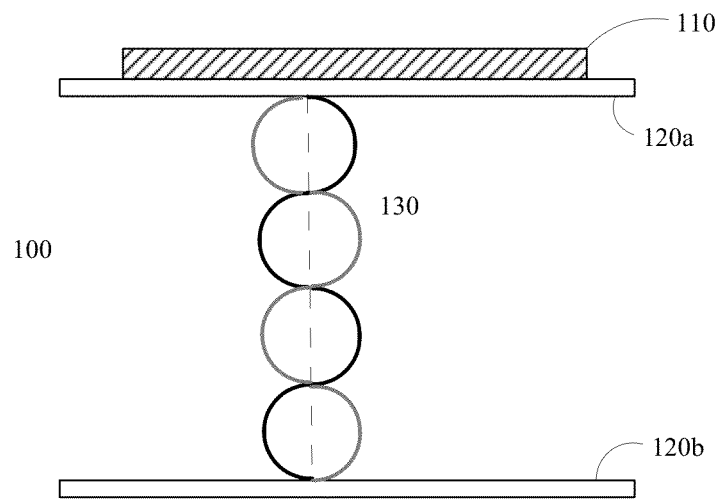
FIG. 1 is a cross sectional representation of a parallel plate standing wave resonator structure.
Figure 2:
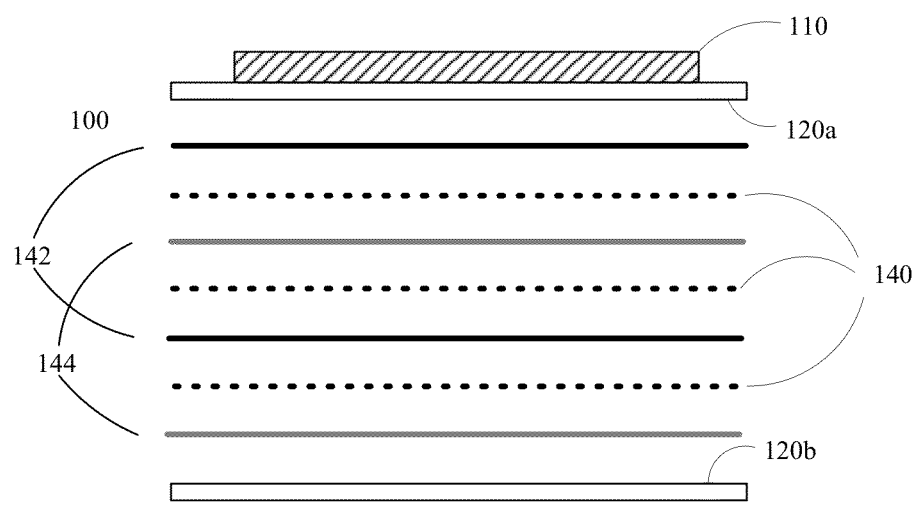
FIG. 2 is a cross sectional representation of a parallel plate standing wave resonator structure depicting the regions of no particle velocity fluctuation (nodes) and maximal particle velocity fluctuation (anti-nodes).
Figure 3:
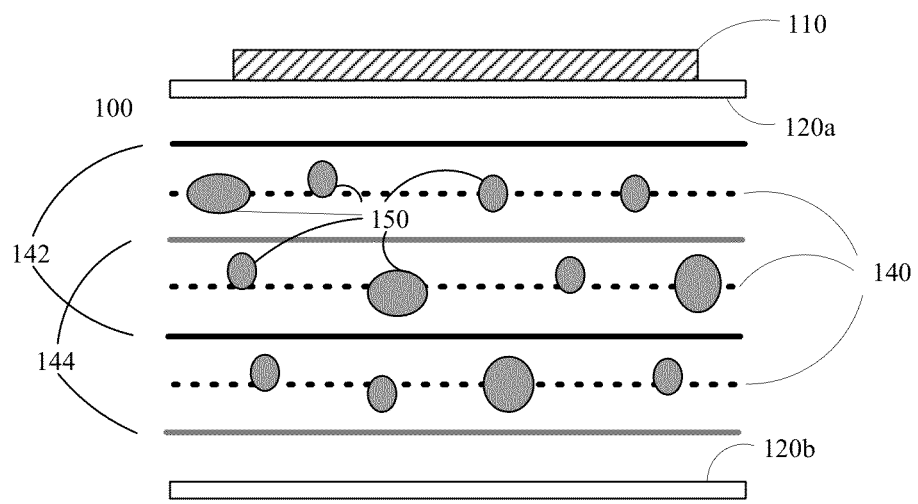
FIG. 3 is a cross sectional representation of a parallel plate standing wave resonator structure depicting the regions of no particle velocity fluctuation (nodes) and maximal particle velocity fluctuation (anti-nodes), including representations of adipose or other cells of a size less than the distance between nodal and anti-nodal regions.

Embodiments of the present invention rely on acoustic standing waves to create forces which preferentially affect cells larger than a predetermined, desired size. By controlling the standing wave pattern, the cells which are of a sufficient size to straddle a nodal region (region of minimal pressure or particle velocity) are be affected by the two adjacent antinodal regions and can be lysed.

In an ultrasonic standing wave field, particles, or in the present instance, cells, experience acoustic radiation forces. The primary radiation force originates from pressure and velocity fluctuations of the molecules of the medium. In an ultrasonic standing wave field, acoustic radiation force moves particles toward the pressure nodes or antinodes depending on the acoustic contrast factor "$\phi$," a function of density and compressibility of the particles and the medium.

The force on a particle (e.g., cell) of radius "r" can be given by:

$$F_{PRF} = -\left(\frac{2\pi^2 p_0^2 r^3 \beta_m}{3\lambda}\right)\phi(\beta,\rho)\sin(2kx)$$

where "$p_o$" is the acoustic pressure amplitude; "$\lambda$" is the wavelength of the acoustic wave, "k" is the wave number; "$\beta_p$" and "$\beta_m$" are the compressibilities of the particle (cell) and medium, respectively, "$\rho_p$" and "$\rho_m$" are the densities of the particle and medium, respectively. The acoustic contrast factor is given by:

$$\phi(\beta,\rho) = \frac{5\rho_p - 2\rho_m}{2\rho_p + \rho_m} - \frac{\beta_p}{\beta_m}$$

Therefore, particles with different acoustic properties will move to different positions (the nodes and antinodes) and can be separated with help of a laminar flow in an ultrasound separation device. The goal in embodiments is to exploit the fact that cells which are large compared to the node to antinode distance will be subjected to high differential forces as well. Thus, cells above a certain size can be lysed. Because these large cells contain primarily lipid, they are a different density than the smaller cells which have less lipid content and proportionally more internal cellular structures. Thus there will be a differential force applied to the different cells. This is in addition to the shear forces that would be induced because the large cells would span the nodal location.

Device 100 shown in FIGS. 1-4 illustrates one embodiment of a device for selectively lysing adipose cells. As used herein, "selectively," "selectivity," or "selective" means, in general, that the ultrasonic lysing results in an adipose tissue mass (e.g., liquid with mixture of cells) more concentrated in small cells than was the original mass. The exact extent of the selectivity depends on the design of the individual lysing device and the extent and technique of operation as employed on a specific adipose mass. In each instance, however, the lysing will result in preferential lysing of cells with a diameter above the predetermined size. In some instances, that may result in minimal, if any, lysing of cells with a diameter below the predetermined size. In other instances, there may be a significant lysing of cells with a diameter below the predetermined size. But in each instance, lysing is more effective with respect to cells having a diameter above the predetermined size than with a diameter below the predetermined size.

Figure 4:
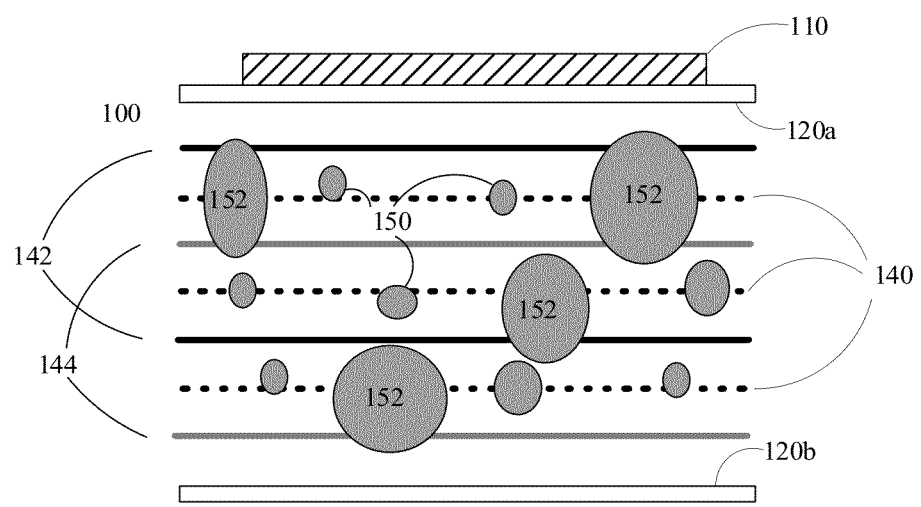
FIG. 4 is a cross sectional representation of a parallel plate standing wave resonator structure depicting the regions of no particle velocity fluctuation (nodes) and maximal particle velocity fluctuation (anti-nodes), including representations of adipose or other cells of a size as great as or greater than the distance between nodal and anti-nodal regions.
Figure 5:
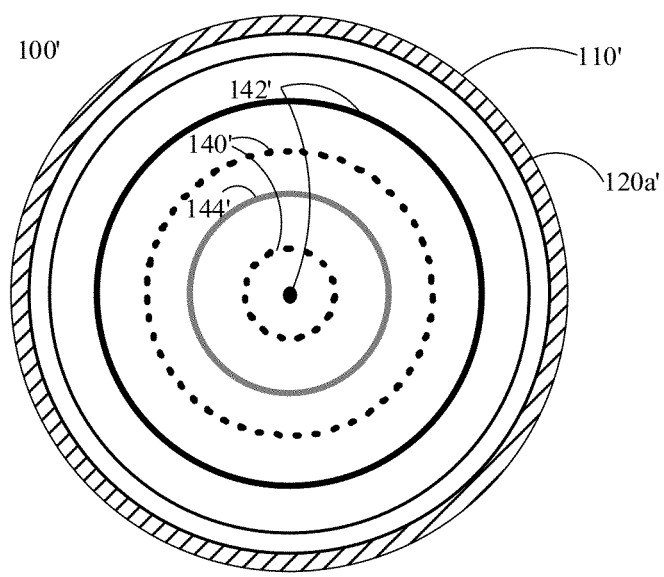
FIG. 5 is an end view representation of a tubular standing wave resonator structure depicting the regions of no particle velocity fluctuation (nodes) and maximal particle velocity fluctuation (anti-nodes).

Referring again to device 100, in use, an aqueous solution containing a mix of adipose or other cells of a variety of sizes would flow through the device 100, between a bottom surface of plate 120a and a top surface of plate 120b. In the embodiment shown in FIG. 1, plates 120a and 120b are parallel. With respect to FIG. 2, 3 or 4, the flow would be, for instance, from left to right. With respect to FIG. 5, the flow would be along the central axis of the cylinder defined by sidewall 120a'. The transducer 110 would generate an acoustic wave that is transmitted through a first surface and would generate an acoustic standing wave field. The acoustic wave may be an ultrasonic wave, which creates an ultrasonic standing wave field. As the aqueous solution containing the mix of adipose or other cells passed through the acoustic standing wave field, those cells which were large enough to straddle the nodal planes (e.g., cells 152), as shown in FIG. 4, would be subject to high shear forces on their cell membranes, caused by the pressure and particle velocity gradients from anti-node to anti-node. The shear forces lead to cell damage or cell death. Other cells, smaller than those just described (e.g., cells 150), would pass through the acoustic standing wave field relatively unaffected by the pressure and velocity gradients. Small cells in a large cluster would also be unaffected because the shear forces would merely break up the cluster, leaving the individual cells intact.

Different size cells may be destroyed by changing the geometry and acoustic working frequency of the device. The distance 130 between the bottom surface of plate 120a and the top surface of 120b must be an integral number of wavelengths of the acoustic standing wave field, as can be appreciated from FIG. 1. The wavelength of the acoustic wave is related to the operating frequency by the equation $\lambda = c/f$, where "$\lambda$" is the wavelength, "c" is the speed of sound in the aqueous medium, and "f" is the operating frequency. The distance between the bottom surface of plate 120a and the top surface of plate 120b (or in the alternate embodiment, the diameter of the cylinder formed from sidewall 120a') is in embodiments an exact integer multiple of the wavelength in order to create a standing wave pattern. Further, the distance can be increased to any reasonable integral number of wavelengths. The larger the distance, the more volume flow can be achieved, and therefore, the larger throughput. However, the acoustic waves will be attenuated and absorbed as they traverse the distance from the bottom surface of plate 120a to the top surface of plate 120b, so that the destructive effect will be lessened if the distance is too great.

Another issue to be considered in the design of device 100 for a particular application is the dwell time, or the time that any specific adipose or other cell would be within the acoustic standing wave field. This clearly depends upon the speed of the cells through the acoustic standing wave field (which is linked to the flow rate), as well as the longitudinal extent of the standing wave (which is determined by the size of the transducer 110). The longer the dwell time, the more complete the process will be in affecting cells above the desired size.

Figure 8:
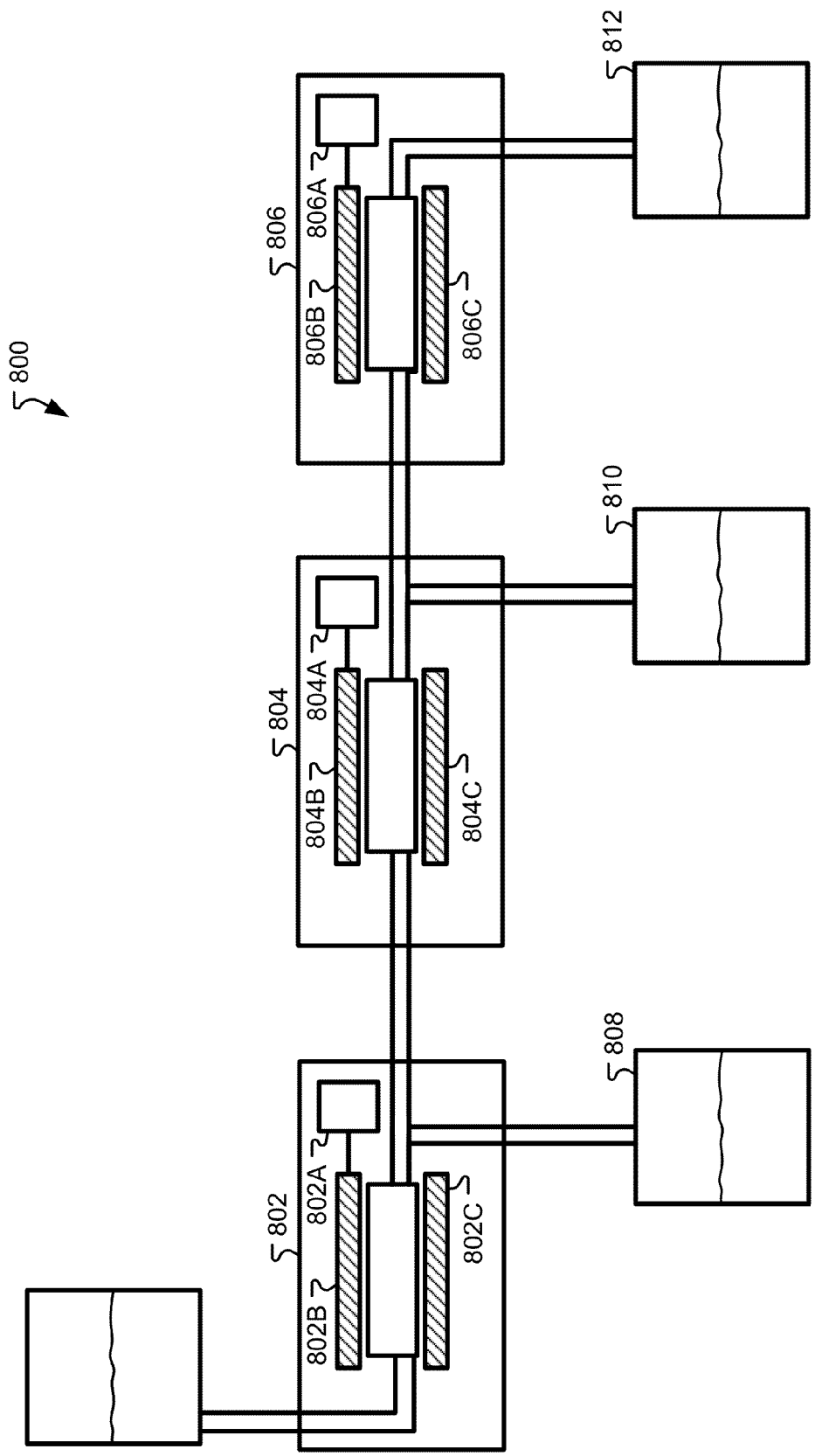
FIG. 8 is a perspective view of a system for lysing adipocytes that includes a number of chambers according to an embodiment of the present invention.

In some embodiments, the device, may include a series of chambers interconnected such that the cellular material passes sequentially through them. FIG. 8 illustrates an embodiment 800 with a series of chambers 802, 804, and 806 each of which is designed to lyse cells of different diameters. The cells would be transported through the series of chambers 802, 804, and 806, starting with one designed to lyse the largest expected cell size, e.g., 802. Subsequent chambers 804 and 806 would be designed for progressively smaller cells. As shown in FIG. 8, each chamber includes a transducer (802A, 804A, and 806A) connected to a first plate (802B, 804B, and 806B) with top and bottom surfaces, and a second plate (802C, 804C, and 806C) with top and bottom surfaces. An acoustic standing wave field is created between the first plates and the second plates.

The device in FIG. 8 affords several features. First, the aqueous medium is slowly cleared of the largest cells, which tend to absorb sound and therefore can interfere with the acoustic standing wave process if they are substantially larger than the "cut off" size. By removing the largest cells (using the lowest frequency), there is less interference for subsequent, higher frequency chambers 804 and 806. Second, very large cells, or cell clusters, could clog a chamber designed for the smallest "cut off" size, so it would be advantageous to have these clusters or large cells disrupted prior to entering the smallest chamber. Additionally, it may be desirable to have multiple outputs from the system as shown by the containers 808, 810, and 812, for instance, one output would be a mixture of cells below a given size, the size selected to include both adipose cells as well as the smaller pre-adipocytes. A further output may contain only the pre-adipocytes, which are the smallest cells.

As those with skill in the art will appreciate, transducer 110 (or 110', 620, 802A, 804A, and 806A) may be any suitable transducer for generating an acoustic standing wave field. One non-limiting example is a transducer made from a piezoelectric ceramic material, such as lead zirconate titanate (PZT). The properties of the transducer materials can be adjusted to suit the application, and in this design, a so-called "hard" ceramic, with a higher mechanical Q is useful in some embodiments (e.g. DoD Type I or PZT-4 from Morgan Electro Ceramics). This approach minimizes the electrical energy needed by minimizing the internal mechanical and dielectric losses within the ceramic material, transferring most of the energy into the acoustic standing wave field. Those skilled in the art of piezoelectric transducers will appreciate that different materials may be used to suit the necessary design goals, such as cost, electrical characteristics, etc.

Referring again to FIGS. 1-4, the plates 120a and 120b must be in intimate contact with the working fluid in order to create and maintain the acoustic standing wave field. The materials selected for these surfaces must provide for easy cleaning and proper acoustical properties. For example, stainless steel may be used because of its high acoustic reflection coefficient and impermeability and resistance to corrosion.

In one embodiment, a pump (e.g., pump 612 shown in FIG. 6) or other forced flow means is used to create the flow of aqueous solution containing the cellular material through the acoustic standing wave field, rather than using gravity or some other natural flow mechanism. By using a pump, the flow rate can be properly controlled, assuring the proper dwell time for the cellular material within the treatment chamber(s). Because the dimensions of the treatment chamber may constrict the flow, a positive pumping means would generally be required in order to overcome the flow resistance presented by the treatment chamber. In those embodiments that use a pump, it is important that the pumping arrangement be designed so that it does not cause cell lysis, which would negate the desired goal of maintain cell viability for cells below the predetermined size.

The use of an acoustic standing wave field, as used in embodiments of the present invention, is very different from filtering or centrifugation, in that it involves active manipulation of the cells using pressure or particle velocity gradients. Filtering causes large cells to be held back in the filter medium while the smaller cells pass through. However, the filter can become clogged, reducing efficiency. Centrifugation is a batch process which takes additional time to complete. Further, after centrifugation, the desired cells must be drawn off, but there is generally no way to determine where the cells of a certain size are within the centrifugation column.

The approach described herein offers a number of advantages over filtering or centrifugation. Like the filtering approach, the standing wave method allows for flow-through processing. Unlike filtering, the standing wave approach permits a continuous flow, with the possibility of reflow through the device. The centrifugation approach is a batch process, which requires additional handling and manipulation of the cells.

The approach described herein allows device embodiments to be adjusted or tuned for the size of the cell to be destroyed by changing the spacing of the node and anti-nodal zones. This is done by a change in the resonant frequency and the distance between the bottom surface of plate 120a and the top surface of plate 120b. Determining the optimal frequency for a given desired result requires minimal experimentation.

Those of skill in the art familiar with the issue of cell separation are mostly familiar with the established mechanisms of filtration and centrifugation. Most of the work currently being described involves specific variations on these approaches, such as custom designed filtering systems with specific pore sizes and ports for sampling and withdrawing filtered material. Similarly, centrifuges are being designed with holders that can quickly adapt to fat harvesting and injection syringes. None of these approaches involve ultrasound, nor are they designed for the continuous flow approach described herein. The use of ultrasound standing waves is unique and novel in this market.

While the drawings depict two embodiments for the device described herein, one being a parallel plate geometry and the other being a cylindrical geometry, those of skill in the art would readily appreciate that other embodiments are possible. Any geometrical configuration which generates an acoustic standing wave, and which can contain a distribution of cells to be processed would fall within the scope of this disclosure. For instance, it is not necessary that the chamber provide for a "flow through" configuration, and a "batch" process arrangement may be desired for specific applications. In this case, the parallel plate geometry may include a circular transducer geometry, with the opposing, reflecting plate being the bottom of a cylindrical container. For example, cells in suspension may be placed in a cylindrical container, whether tall in aspect ratio (e.g. a graduated cylinder) or short in aspect ratio (e.g. a Petri dish). A circular transducer of diameter slightly less than the diameter of the cell container could be lowered into the container until the distance between the transducer and the bottom of the container satisfied the standing wave criteria noted elsewhere. At that distance, the transducer is energized and the cells are treated. After an appropriate dwell time (determined experimentally for the type of cells to be treated, the total volume to be treated, and the available transducer power), the transducer is turned off and withdrawn, so that there remains a cell suspension with the cells above a certain dimension lysed. This is clearly a "batch" procedure, but would be suitable for controlled laboratory experimentation with small cell volumes.

Once the cells have been treated so as to destroy the cells over a certain size, the suspension can be further processed, depending upon the clinical requirements. The lysed cells will release the lipid material stored within them, so there will be free lipid material dispersed within the cell suspension. Since the free lipid is not as dense as the intact cells or typically the aqueous solution of the cell suspension, the lipids will rise to the top of the suspension, where they are easily drawn off. Further, the cell remnants (e.g., membranes of disrupted cells that have discharged their contents) are denser than the other intact cells (because they no longer contain the lower density lipid material within them), so again, these remnants will settle to the bottom of the cell suspension. The desired cell material can thus be easily distinguished from the other, unwanted material within the aqueous suspension, facilitating its collection for re-implantation.

In some embodiments, after lysing large cells, the solution is subjected to a separation process to separate the smaller intact cells from the cell remnants and other components of the solution. Example separation processes may include one or more of filtration, centrifugation, and settling. These processes may be aided by adding materials, i.e, chemicals, that assist in separating the various components of the solution. As described above, lysing of the larger cells makes the separation processes more effective than if the solution were processed without lysing. Additionally, since the lysed cells have liberated their internal lipid contents, the remnant cellular material is of a much higher density and compressibility than intact cells. This makes them more differentiable with regard to acoustic separation, allowing the process to have a secondary utility. Note that in the design of an overall lysing and separation system, acoustic separation may be accomplished in a second chamber distinct from the chamber which produces cell lysing. A succession of devices, each tuned to a different cell or cluster size, may be used to improve the overall functioning of the system.

In those embodiments in which it is desired to have only stem cells, or pre-adipocytes, the process is essentially the same, save for the determination of the cell diameter to be lysed. Stem cells and pre-adipocytes are smaller and denser than adipocytes. Once the adipocytes have been lysed using the method described herein, the stem cells and pre-adipocytes may be removed using the technique just described, especially since these desired cells contain little or no lipid material.

As a potentially beneficial side effect of this method, the remaining (desired) cells will have been stimulated by the action of the acoustic standing wave field. While the force on these cells should be primarily isotropic, there will be some residual shear stress. These micro-stresses and so-called "micro streaming" around cells can serve to "activate" the cell membranes, allowing for increased biochemical activity and thereby a promotion of cell growth. This is useful regardless of whether the lysing is used to isolate cells for re-insertion or for research or therapeutic use.

In some embodiments, the unlysed cells (adipocytes and stem cells) remaining after lysing are used therapeutically by being reinserted into a patient. As those with skill in the art will appreciate, these cells can undergo additional processing to prepare the cells for reintroduction. In some embodiments, after the lysing process, the unlysed cells are separated from other components of the liquid and are further processed to stimulate the cells prior to reinsertion into a patient. This further processing may involve a number of biochemical steps that improve the cells' ability to be used therapeutically such as by increasing their activity or longevity.

Figure 6:
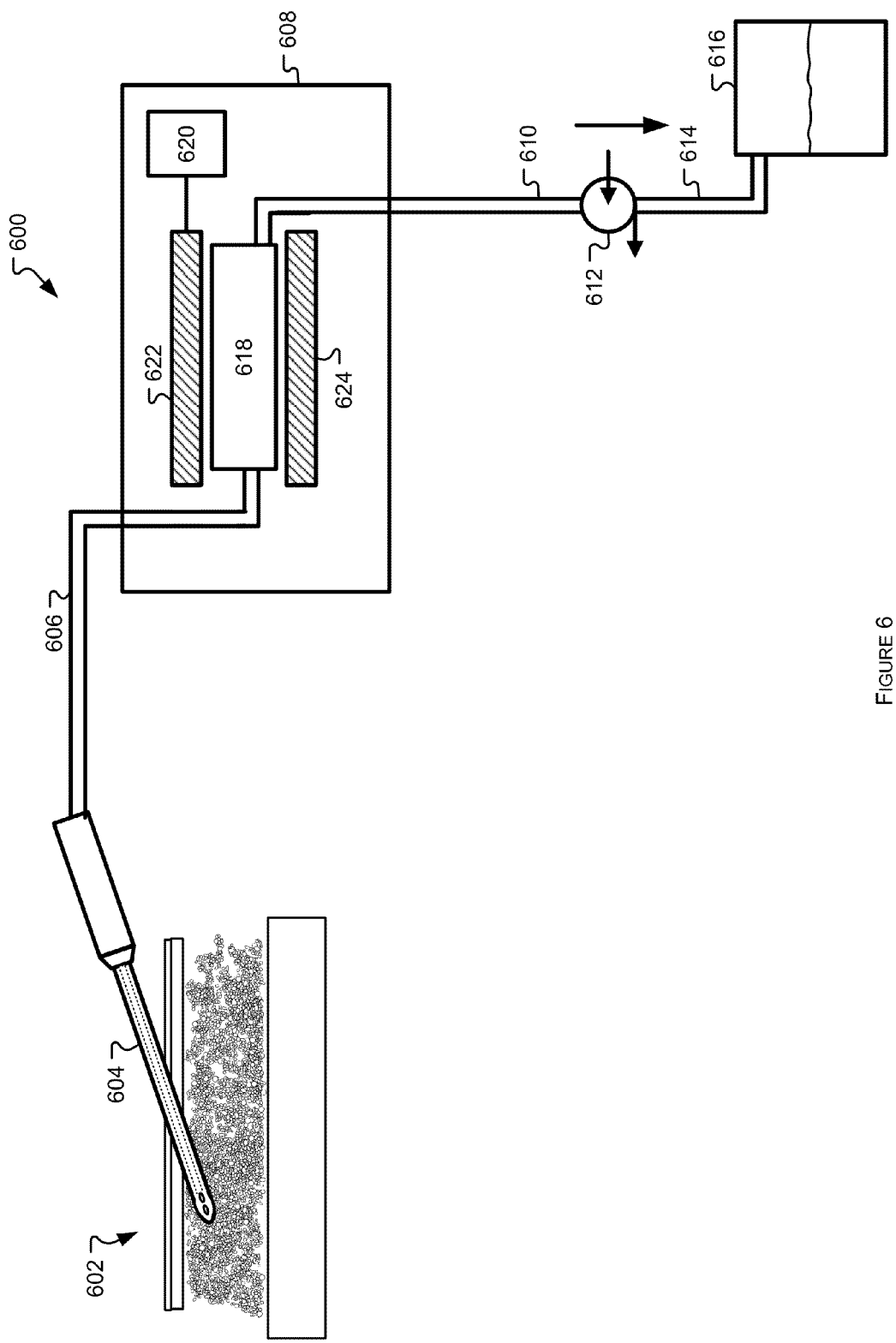
FIG. 6 is a perspective view of a system for lysing adipocytes that includes a cartridge according to an embodiment of the present invention.

System 600 shown in FIG. 6, illustrates a system for harvesting adipocytes and stem cells from a surgical site 602, and processing a solution containing adipocytes and stem cells. System 600 includes a cannula 604 that provides a pathway for removing the adipocytes and stem cells from the surgical site 602. A standing wave resonator device 608 is connected to cannula 604 through tubing 606. Tubing 610 connects standing wave resonator device 608 to a pump 612 The pump 612 is operated to create suction at the tip of cannula 604 causing the adipocytes and stem cells to flow from surgical site 602 through standing wave resonator device 608 and into a reservoir 616 connected to pump 614. The pump 612 is connected to reservoir 616 with tubing 614. The reservoir 616 stores the adipocytes and stem cells for further processing.

As shown in FIG. 6, system 600 provides for in-stream lysing of adipocytes that are in a solution of adipocytes and stem cells. Standing wave resonator device 608 may be any suitable resonator for creating a standing wave, such as the resonator devices described above with respect to FIGS. 1-5. As shown in FIG. 6, device 608 includes a removable cartridge 618. The solution of stem cells and adipocytes is stored within cartridge 618 which acts as a chamber for holding the solution during the process of lysing the larger adipocytes.

The walls of cartridge 618 are acoustically transparent, which allows ultrasonic energy to pass through with minimal interference. Also, cartridge 618 is sealed so that outside contaminants will not enter the interior of the cartridge. In operation, transducer 620 generates an acoustic wave that is transmitted through a first surface of plate 622 and generates an acoustic standing wave field between plates 622 and 624. As a result of the acoustically transparent nature of cartridge 618, the standing wave is created and maintained within the removable cartridge 618. As the solution containing the mix of adipocytes, stem cells, and or fluids passes through removable cartridge 618, those cells which are large enough to straddle the nodal planes as shown in FIG. 4, are subject to high shear forces on their cell membranes, caused by the pressure and particle velocity gradients from anti-node to anti-node. The shear forces lead to cell damage or cell death. Other cells would pass through the removable cartridge 618 relatively unaffected by the pressure and velocity gradients.

Removable cartridge 618 provides a convenient way to ensure the sterility of the environment during lysing. In some embodiments, cartridge 618 is disposable, so that each time device 608 is used; removable cartridge 618 is replaced with a new cartridge. In other embodiments, cartridge 618 may be reposable meaning that it must be sterilized prior to reuse. However, because removable cartridge 618 is designed to be easily removed from device 608, it can easily be removed from device 608 and sterilized without being connected to other components of device 608.

As shown in the embodiment of FIG. 6, the solution of adipocytes and stem cells does not directly contact any portion of device 608 except for cartridge 618. The solution flows through tubing 606, cartridge 618, and tubing 610. The other components of device 608 are used to generate the standing wave but do not come in contact with the solution of adipocytes and stem cells. For this reason, in some embodiments, tubing 606, cartridge 618, and tubing 610 are disposable and used only one time.

Figure 7:
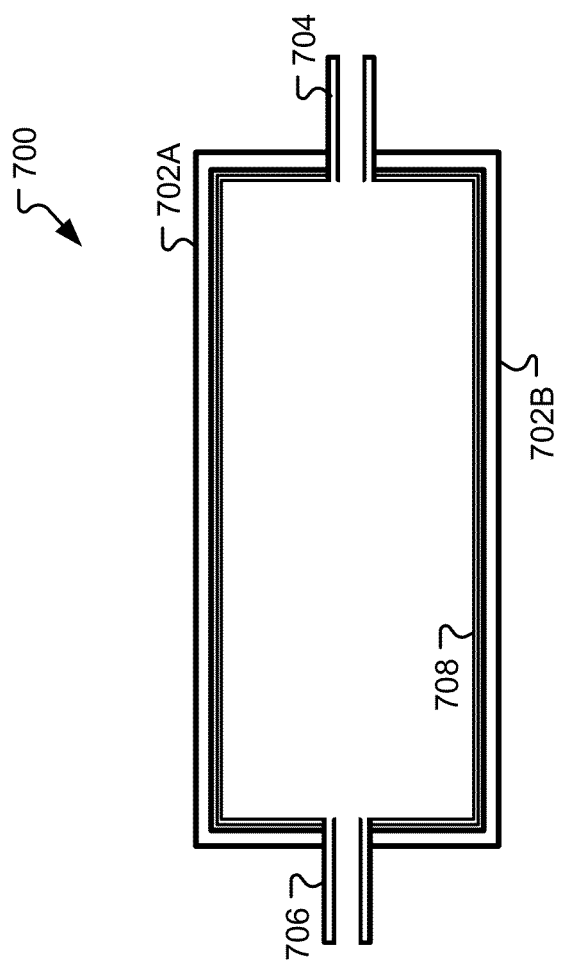
FIG. 7 is a cross-sectional view of a cartridge that may be used in the system shown in FIG. 6.

FIG. 7 illustrates a cross-sectional view of an embodiment of a cartridge 700 that may be used as cartridge 618 in system 600 (FIG. 6). Cartridge 700 includes walls 702A and 702B, which are acoustically transparent. That is, they allow sound waves, e.g., ultrasonic sound waves, to be transmitted through them with little or no interference. This allows a standing wave to be created in the interior of cartridge 700. Those with skill in the art will appreciate that acoustically transparent materials that are suitable for this application include without limitation plastics, such as REXOLITE® a cross linked polystyrene microwave plastic made by C-Lec Plastics, Inc. Philadelphia, Pa. The particular type of material used may be selected based on the exact frequency of the acoustic wave, the chemical composition of the solution that includes the adipocytes and stem cells, and other environmental factors such as whether the cartridge is disposable or reposable and will be sterilized in an autoclave.

Cartridge 700 also includes connections 704 and 706 that allows cartridge 700 to be inserted into the flow path of a solution that includes adipocytes and stem cells. Connections 704 and 706 may in some embodiments be conventional connections that allow cartridge 700 to connect to, for example, tubing. The connections 704 and 706 may include threads, clamps, knobs, or other types of fasteners/connectors. In addition to the features that allow cartridge 700 to connect to a flow path of a solution of adipocytes and stem cells, connectors 704 and 706 may also include connectors that allow cartridge 700 to be secured within a wave resonator device, such as those devices described above in FIGS. 1-6.

In some embodiments, cartridge 700 also includes an interior coating 708 that is applied to the interior walls of cartridge 700. The coating 708 may be a membrane, a continuous layer, or a discontinuous layer. The coating may include any number of materials that are useful for processing the solution of adipocytes and stem cells. For example, the coating 708 may include chemicals that assist in destroying the cell membranes of the larger adipocytes during the lysing process. Other examples include chemicals that prolong the life of the cells in solution or that assist in breaking up groups of cells. The coating 708 may also provide a barrier to contaminants

VII. EXAMPLES

Example 1

As a design example, assume that it is desired to preferentially affect cells at or above 250 microns (0.250 mm) in diameter. Thus the distance between the anti-nodal planes 142 and 144 would be set to 250 microns. The nodal planes are illustrated as 140. From this, the wavelength of the acoustic standing wave field would be 0.5 mm. Assuming a speed of sound in the aqueous medium of 1500 m/s (similar to that of water), then the frequency of operation is 3 MHz. Numerous transducers of different sizes, dimensions, and power handling capabilities are available at this frequency. The distance between the bottom surface of plate 120*a* and the top surface of plate 120*b* would then need to be an integral number of wavelengths, for example 1.0, 1.5, 2.0, 2.5 mm, etc. The distance between the plates also affects the total flow through the device 100, as a larger distance allows more fluid to flow through, assuming a constant transit velocity for the aqueous solution containing the cells.

What is claimed is:

1. A method for lysing adipose cells of diameters equal to or greater than a predetermined diameter, the method comprising:
   generating an acoustic standing wave field, wherein the geometry of the acoustic standing wave field is such that one half of the wavelength of the acoustic standing wave field is less than or equal to the predetermined diameter, and wherein the intensity of the acoustic standing wave field is sufficient to cause lysing of adipose cells of diameters equal to or greater than the predetermined diameter; and
   subjecting a mixture of adipose cells and stem cells to the acoustic standing wave field to generate a lysed mixture, wherein the mixture of adipose cells and stem cells includes at least some adipose cells having a diameter equal to or greater than the predetermined diameter.

2. The method of claim 1, wherein the subjecting results in selective lysing of adipose cells equal to or greater than the predetermined diameter compared to cells of a smaller diameter.

3. The method of claim 1, wherein the acoustic standing wave field is an ultrasonic standing wave field.

4. The method of claim 1, further comprising:
   processing the lysed mixture to prepare at least a portion of the lysed mixture for injection into a patient.

5. The method of claim 4, wherein the processing comprises:
   a separation process that separates intact cells from other components of the lysed mixture, the separation process comprising at least one of: filtration, centrifugation, and settling.

6. The method of claim 1, wherein the subjecting comprises holding a batch of the mixture in a chamber that includes the acoustic standing wave field for a preset dwell time.

7. The method of claim 1, wherein the subjecting comprises:
   flowing the mixture through a chamber that includes the acoustic standing wave field.

8. The method of claim 1, wherein the method further comprises lysing adipose cells of diameters equal to or greater than a second predetermined diameter that is smaller than the first predetermined diameter by:
   generating a second acoustic standing wave field, wherein the geometry of the second acoustic standing wave field is such that one half of the wavelength of the second acoustic standing wave field is less than or equal to the second predetermined diameter, and wherein the intensity of the second acoustic standing wave field is sufficient to cause lysing of adipose cells of diameters equal to or greater than the second predetermined diameter; and
   subjecting the lysed mixture to the second acoustic standing wave field, wherein the lysed mixture includes at least some adipose cells having a diameter equal to or greater than the second predetermined diameter.

9. A method for lysing adipose cells of diameters equal to or greater than a predetermined diameter, the method comprising:
   generating an acoustic standing wave field, wherein the geometry of the acoustic standing wave field is such that one half of the wavelength of the acoustic standing wave field is less than or equal to the predetermined diameter, the wavelength of the acoustic standing wave field falling within a range of 0.5 mm to 2.5 mm, and wherein the intensity of the acoustic standing wave field is sufficient to cause lysing of adipose cells of diameters equal to or greater than the predetermined diameter; and
   subjecting a mixture of adipose cells and stem cells to the acoustic standing wave field to generate a lysed mixture, wherein the mixture of adipose cells and stem cells includes at least some adipose cells having a diameter equal to or greater than the predetermined diameter.

10. The method of claim 9, wherein the subjecting results in selective lysing of adipose cells equal to or greater than the predetermined diameter compared to cells of a smaller diameter.

11. The method of claim 9, wherein the acoustic standing wave field is an ultrasonic standing wave field.

12. The method of claim 9, further comprising:
processing the lysed mixture to prepare at least a portion of the lysed mixture for injection into a patient.

13. The method of claim 12, wherein the processing comprises:
a separation process that separates intact cells from other components of the lysed mixture, the separation process comprising at least one of: filtration, centrifugation, and settling.

14. The method of claim 9, wherein the subjecting comprises holding a batch of the mixture in a chamber that includes the acoustic standing wave field for a preset dwell time.

15. The method of claim 9, wherein the subjecting comprises:
flowing the mixture through a chamber that includes the acoustic standing wave field.

16. The method of claim 9, wherein the method further comprises lysing adipose cells of diameters equal to or greater than a second predetermined diameter that is smaller than the first predetermined diameter by:
generating a second acoustic standing wave field, wherein the geometry of the second acoustic standing wave field is such that one half of the wavelength of the second acoustic standing wave field is less than or equal to the second predetermined diameter, and wherein the intensity of the second acoustic standing wave field is sufficient to cause lysing of adipose cells of diameters equal to or greater than the second predetermined diameter; and
subjecting the lysed mixture to the second acoustic standing wave field, wherein the lysed mixture includes at least some adipose cells having a diameter equal to or greater than the second predetermined diameter.

\* \* \* \* \*